(12) United States Patent
Marciniak et al.

(10) Patent No.: US 12,023,442 B2
(45) Date of Patent: **\*Jul. 2, 2024**

(54) INTUBATING AIRWAY FOR BRONCHOSCOPIC TRACHEAL INTUBATIONS

(71) Applicant: THE CLEVELAND CLINIC FOUNDATION, Cleveland, OH (US)

(72) Inventors: Donn Marciniak, Cleveland, OH (US); Erik Kraenzler, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/075,495

(22) Filed: Dec. 6, 2022

(65) Prior Publication Data

US 2023/0099657 A1    Mar. 30, 2023

Related U.S. Application Data

(63) Continuation of application No. 16/326,406, filed as application No. PCT/US2017/047729 on Aug. 21, 2017, now Pat. No. 11,541,196.

(60) Provisional application No. 62/377,015, filed on Aug. 19, 2016.

(51) Int. Cl.
  *A61M 16/04* (2006.01)
  *A61B 1/00* (2006.01)
  *A61B 1/267* (2006.01)

(52) U.S. Cl.
  CPC ..... *A61M 16/0488* (2013.01); *A61B 1/00165* (2013.01); *A61B 1/2673* (2013.01); *A61M 16/0463* (2013.01)

(58) Field of Classification Search
  CPC .......................................... A61M 16/04–0468
  See application file for complete search history.

(56) References Cited

U.S. PATENT DOCUMENTS

| 3,903,507 A | 9/1975 | Dillingham |
| 4,068,658 A | 1/1978 | Berman |
| 4,338,930 A | 7/1982 | Williams |
| 5,024,218 A | 6/1991 | Ovassapian et al. |
| 5,069,206 A | 12/1991 | Crosbie |
| 7,866,313 B2 | 1/2011 | Isenberg et al. |
| 10,413,689 B2 | 9/2019 | Eaton et al. |
| 2002/0040712 A1 | 4/2002 | Chou |
| 2009/0013995 A1 | 1/2009 | Williams |

OTHER PUBLICATIONS

International Search Report dated Nov. 27, 2017 for corresponding International Application No. PCT/US2017/047729 filed Aug. 21, 2017.

*Primary Examiner* — LaToya M Louis
(74) *Attorney, Agent, or Firm* — TAROLLI, SUNDHEIM, COVELL & TUMMINO L.L.P.

(57) ABSTRACT

An intubating airway can include a first having a first guiding surface and a second articulating component that is attached to the first component via a hinge and has a second guiding surface. In a closed configuration, the first and second guiding surfaces can be flush with one another so that the first and second components collectively define a conduit having an interior passage that is dimensioned to direct a fiber-optic scope or an endotracheal tube extending through the interior passage for tracheal intubation. In an open configuration, the first and second guiding surfaces are not flush with one another so that no such conduit is formed.

20 Claims, 13 Drawing Sheets

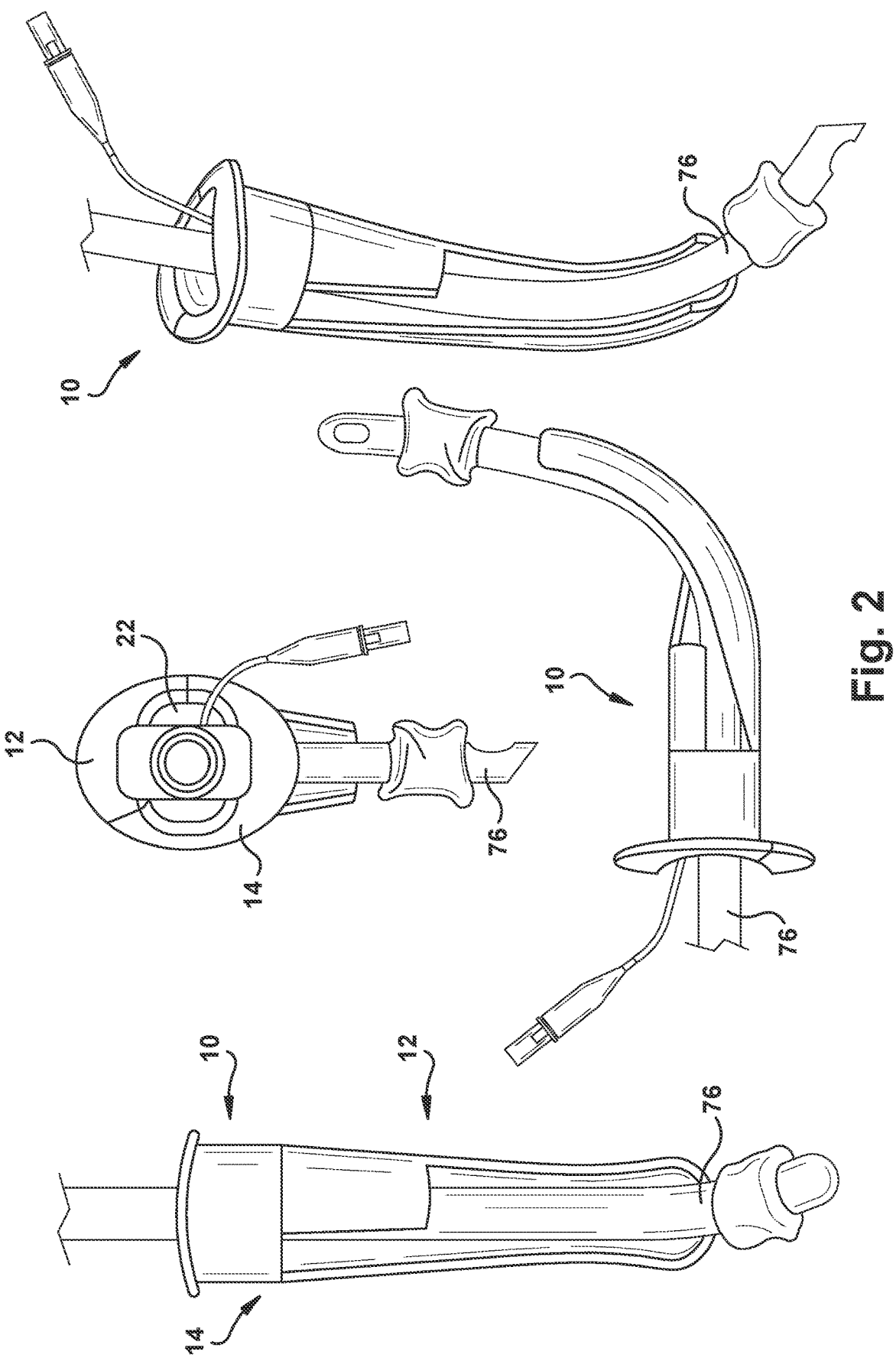

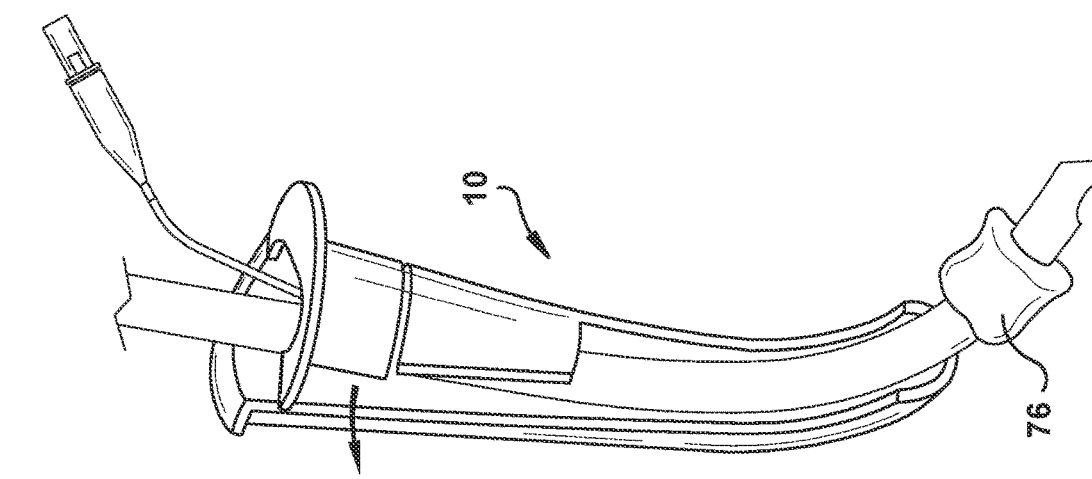
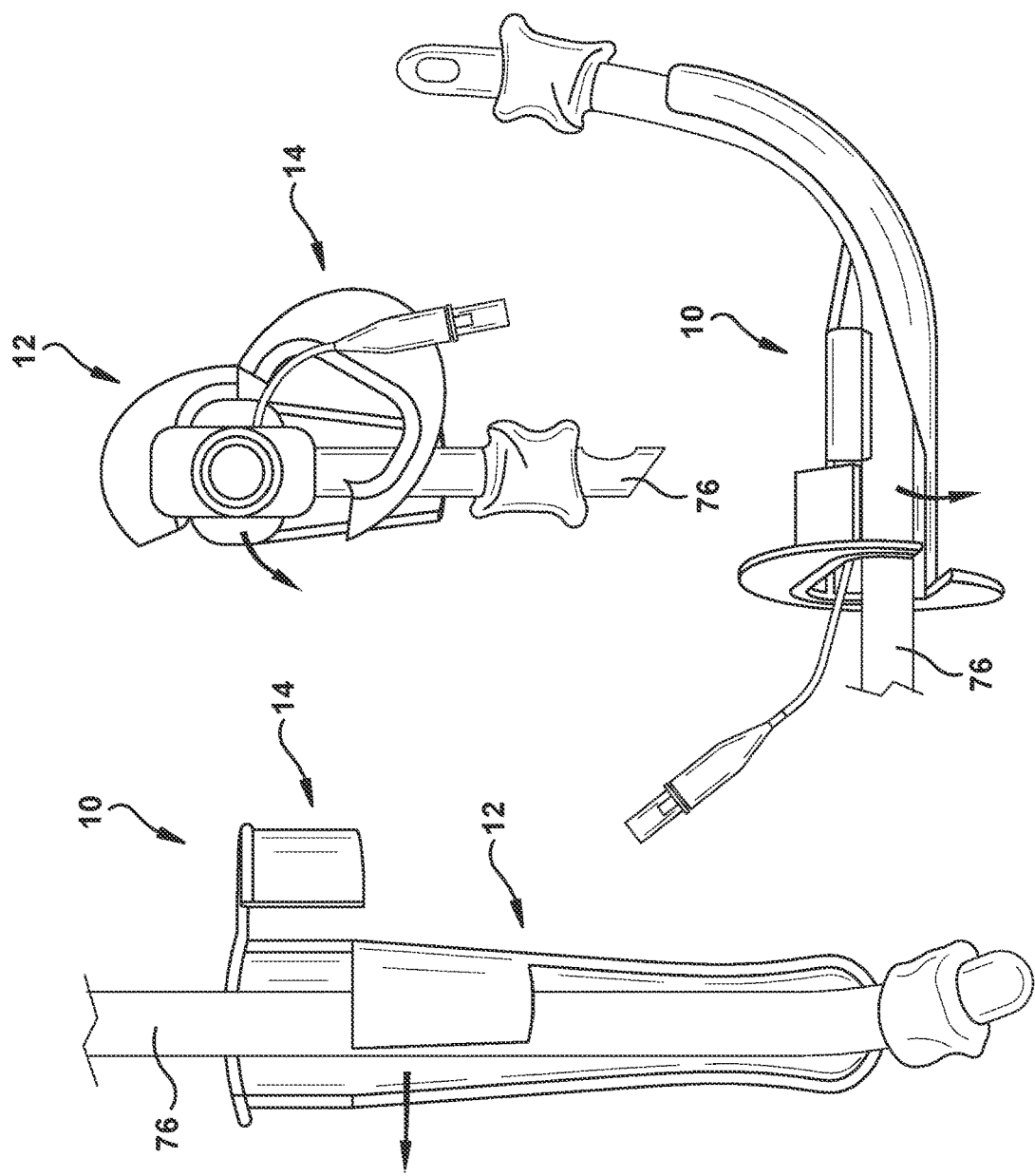
Fig. 3

INTUBATING AIRWAY FOR BRONCHOSCOPIC TRACHEAL INTUBATIONS

RELATED APPLICATION

This application is a continuation of U.S. patent application Ser. No. 16/326,406, filed Feb. 19, 2019, which is a 371 of PCT/US2017/047729, filed Aug. 21, 2017, which claims the benefit of U.S. Provisional Patent Application Ser. No. 62/377,015, filed Aug. 19, 2016, the entirety of each application is hereby incorporated by reference for all purposes.

TECHNICAL FIELD

The present disclosure relates generally to oral airways and, in particular to oral airways that facilitate fiber-optic intubation of the trachea.

BACKGROUND

Oral airways are well known. Generally, an oral airway is a device used in anesthesia to maintain patency of the path from the mouth of a patient to the pharynx of the patient. Oral airways are commonly utilized to facilitate mask ventilation in a variety of clinical settings.

One use of oral airways is to facilitate fiber-optic intubation of the trachea with an endotracheal tube. The oral airway splints open the mouth providing a conduit through which a thin filamentous fiber-optic bronchoscope may be passed from the mouth through the vocal cords so that, in turn, an endotracheal tube may be passed over the fiber-optic scope through the oral airway to the proper position through the vocal cords.

The basic design of conventional oral airways in use today is that of a hollow plastic tube which, when placed between the teeth, functions as a bite block and follows a natural curve to the posterior pharynx to facilitate passage of a fiber-optic tube bronchoscope through the vocal cords.

SUMMARY

The present disclosure relates generally to oral airways and, in particular to oral airways that facilitate fiber-optic intubation of the trachea.

One aspect of the present disclosure relates to an intubating airway. The intubating airway can comprise a first guiding surface and a second articulating component that is attached to the first component via a hinge and has a second guiding surface. In a closed configuration, the first and second guiding surfaces can be flush with one another so that the first and second components collectively define a conduit having an interior passage that is dimensioned to direct a fiber-optic scope (e.g., a bronchoscope) or an endotracheal tube extending through the interior passage for tracheal intubation. In an open configuration, the first and second guiding surfaces are not flush with one another so that no such conduit is formed.

Another aspect of the present disclosure relates to an intubating airway intended to facilitate the guidance and insertion of an endotracheal tube using a fiber-optic scope (e.g., a bronchoscope). The intubating airway can comprise a first component and a second articulating component. The first component can comprise a proximal portion and a distal portion. The proximal portion can extend generally linearly in a longitudinal direction. The proximal portion can include at a first end thereof a flat vertical face defining at least a portion of a mouth guard of the oral airway. The distal portion can be integral with the proximal portion and extend therefrom in a curved manner. The component can be attached to the proximal portion at a hinge. In a closed configuration, the first and second guiding surfaces can be flush with one another so that the first and second components collectively define a conduit having an interior passage that is dimensioned to direct a fiber-optic scope or an endotracheal tube extending through the interior passage for tracheal intubation. In an open configuration, the first and second guiding surfaces are not flush with one another so that no such conduit is formed. No such interior passage is formed in the open configuration but the first component defines an open-ended channel dimensioned to receive therethrough an endotracheal tube, whereby the intubating airway may be removed from an endotracheal tube extending through the passage without having to pass any portion of the intubating airway over an end of the endotracheal tube.

Another aspect of the present disclosure relates to a method for endoscopic tracheal intubation. One step of the method can include extending a fiber-optic scope (e.g., a bronchoscope) or an endotracheal tube through a conduit defined by a first component and a second articulating component of an intubating airway. The first component can have a first guiding surface and the second component can be attached to the first component via a hinge and have a second guiding surface, wherein the first and second components are in a closed configuration to define the conduit. The intubating airway can be transitioned into an open configuration, after an endotracheal tube has extended through the conduit for tracheal intubation, such that the first and second guiding surfaces are not flush with one another and the conduit is not formed. The intubating airway can be removed from the patient's mouth without disrupting the endotracheal tube.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 2 is a series of illustrations showing an endotracheal tube extending through the intubating airway of FIG. 1A;

FIG. 3 is a series of illustrations showing an endotracheal tube extending through the intubating airway of FIG. 1B;

DETAILED DESCRIPTION

Definitions

Figure 1A:
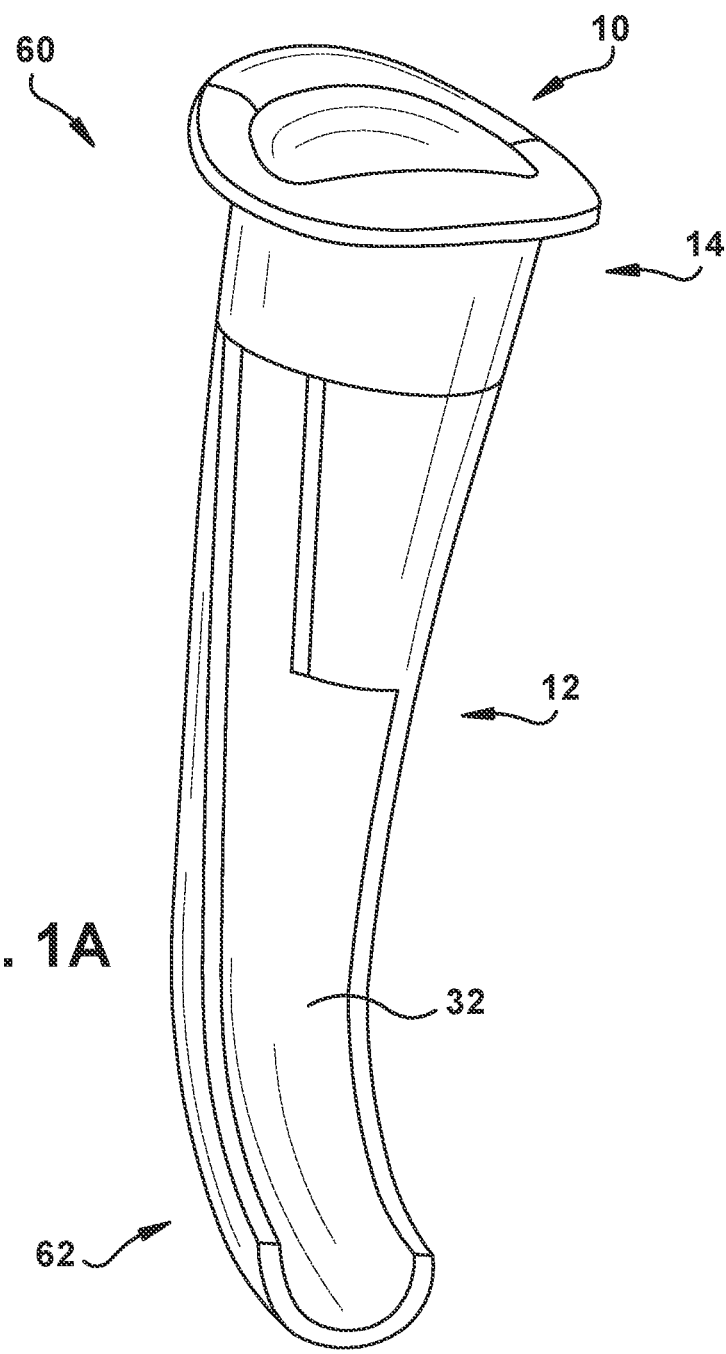
FIG. 1A is a perspective view showing an intubating airway in a closed-configuration according to one aspect of the present disclosure.

Unless defined otherwise, all technical and scientific terms used herein have the same meaning as is commonly understood by one of skill in the art to which the present disclosure pertains.

In the context of the present disclosure, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

As used herein, phrases such as "between X and Y" and "between about X and Y" can be interpreted to include X and Y.

As used herein, phrases such as "between about X and Y" can mean "between about X and about Y."

As used herein, phrases such as "from about X to Y" can mean "from about X to about Y."

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of the apparatus in use or operation in addition to the orientation depicted in the figures. For example, if the apparatus in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

As used herein, the term "fiber-optic scope" can refer to an endoscopic instrument (or an endoscope) that is used for a medical procedure. Non-limiting examples of such instruments can include bronchoscopes, borescopes, fiberscopes, etc., or any tool for performing tasks within an enclosed space viewed using these instruments.

As used herein, the terms "ventilating" or "ventilate" can refer to providing breathable air or oxygen, for example, and removing gas, etc., e.g., exhalant exhaled by a subject, and providing anesthesia and/or other materials to and/or from the lungs of a subject. The terms can also have the usual meaning as used in the field of medicine. The various gases, e.g., oxygen, air, inhaled anesthetic agents, etc., alone or in combination sometimes are referred to below collectively as a gas mixture.

As used herein, the terms "subject" and "patient" can be used interchangeably and refer to any warm-blooded organism including, but not limited to, human beings, pigs, rats, mice, dogs, goats, sheep, horses, monkeys, apes, rabbits, cattle, etc.

Overview

The present disclosure relates generally to oral airways and, in particular to oral airways that facilitate fiber-optic intubation of the trachea. Bronchoscope intubations are a sub-set of a typical airway intubation that are used when a patient has a condition, disease state or oral/pharyngeal physiology that makes a traditional intubation and subsequent breathing tube placement impossible. These patients are at high risk for airway loss during the procedure. This can lead to life-threatening conditions of asphyxiation and associated morbidities, and requires an emergency tracheotomy. Conventional oral airways, such as the Williams and Ovassapian airways, having limited functionality in such procedures as they do not permit airway device removal without disruption of the placed endotracheal tube—a complication that can jeopardize the procedure and patient safety. The Williams airway, for example, cannot be removed unless it is done so over the placed endotracheal tube, which increases the risk of extubation. The Ovassapian airway can be crushed and does not protect the oropharynx. Advantageously, the present disclosure provides an intubating airway that overcomes the limited functionality of conventional oral airways by including an articulating channel and bite block that permits the intubating airway to be removed from an endotracheal tube without disrupting its placement. This and other advantages of the intubating airway of the present disclosure are discussed below.

Intubating Airway

Figure 1B:
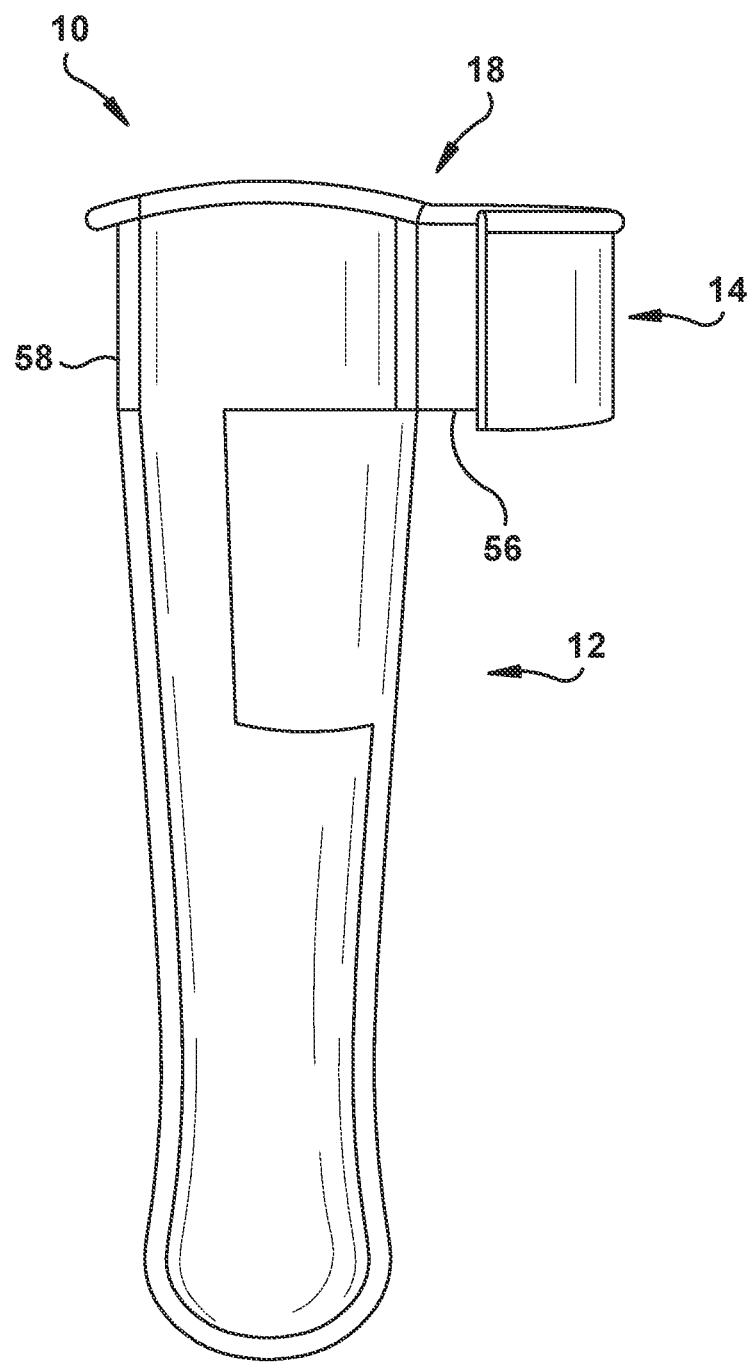
FIG. 1B is a front view showing the intubating airway in FIG. 1A in a closed configuration.
Figure 1C:
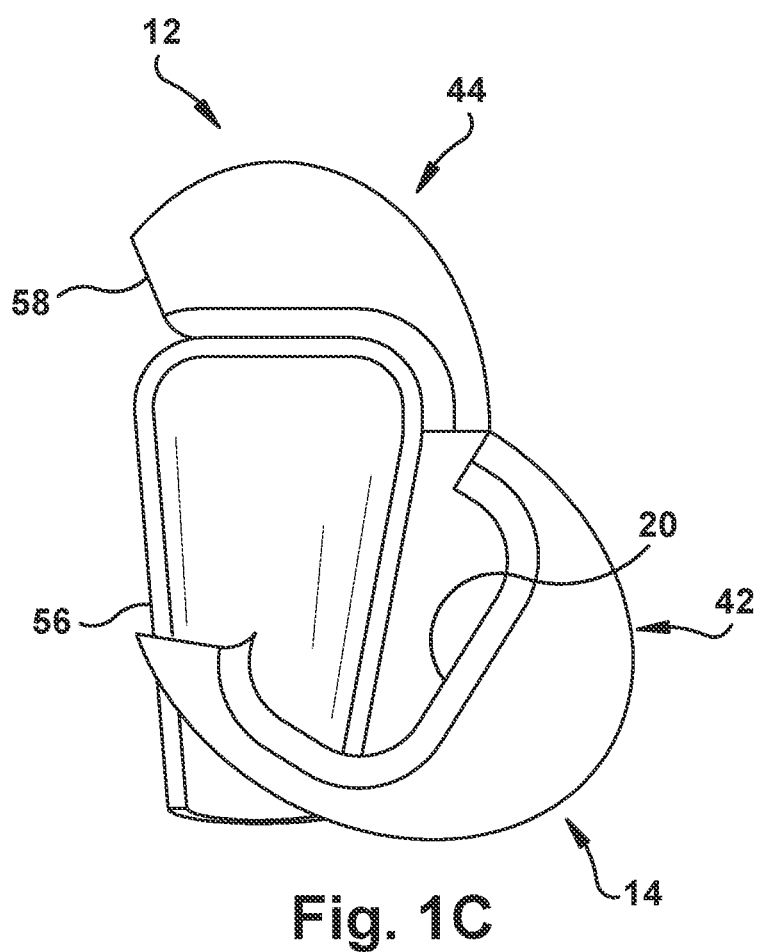
FIG. 1C is a top view of the intubating airway in FIG. 1B.
Figure 4A:
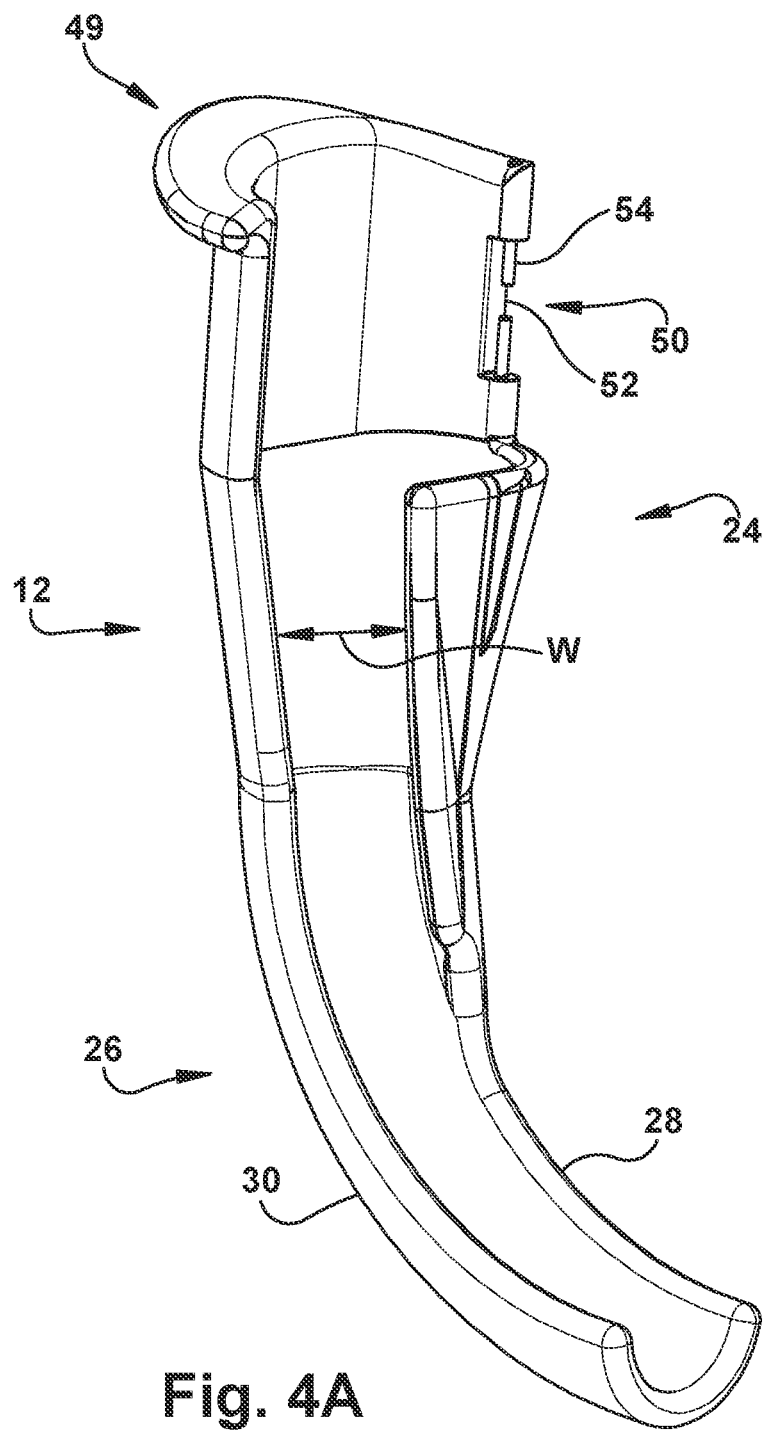
FIG. 4A is a perspective view showing a first component of the intubating airway in FIGS. 1A-C.
Figure 4B:
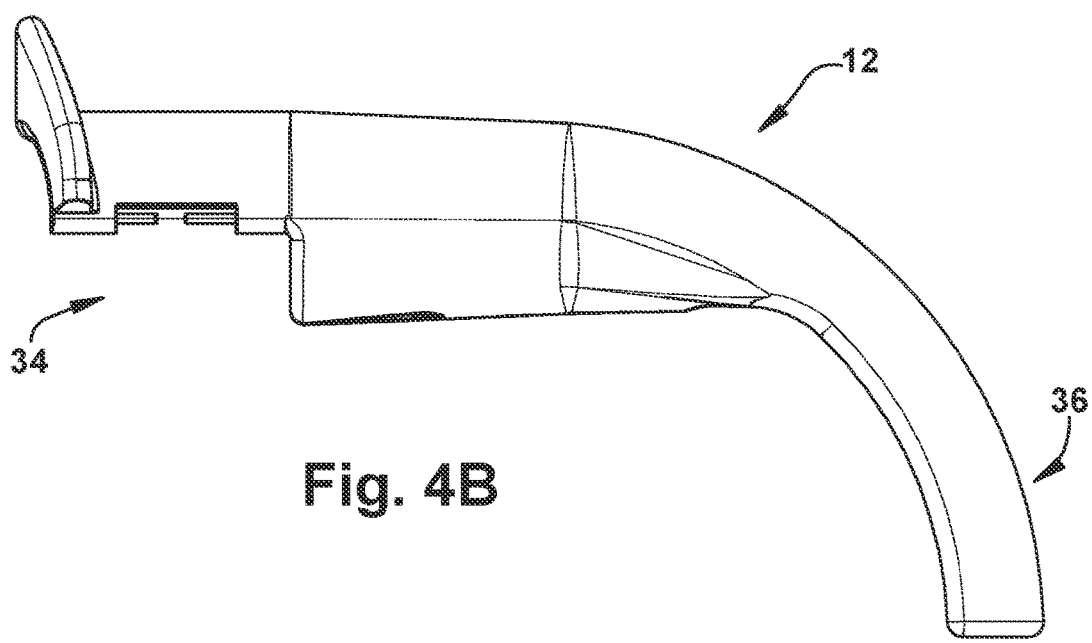
FIG. 4B is a side view showing the first component in FIG. 4A.
Figure 4C:
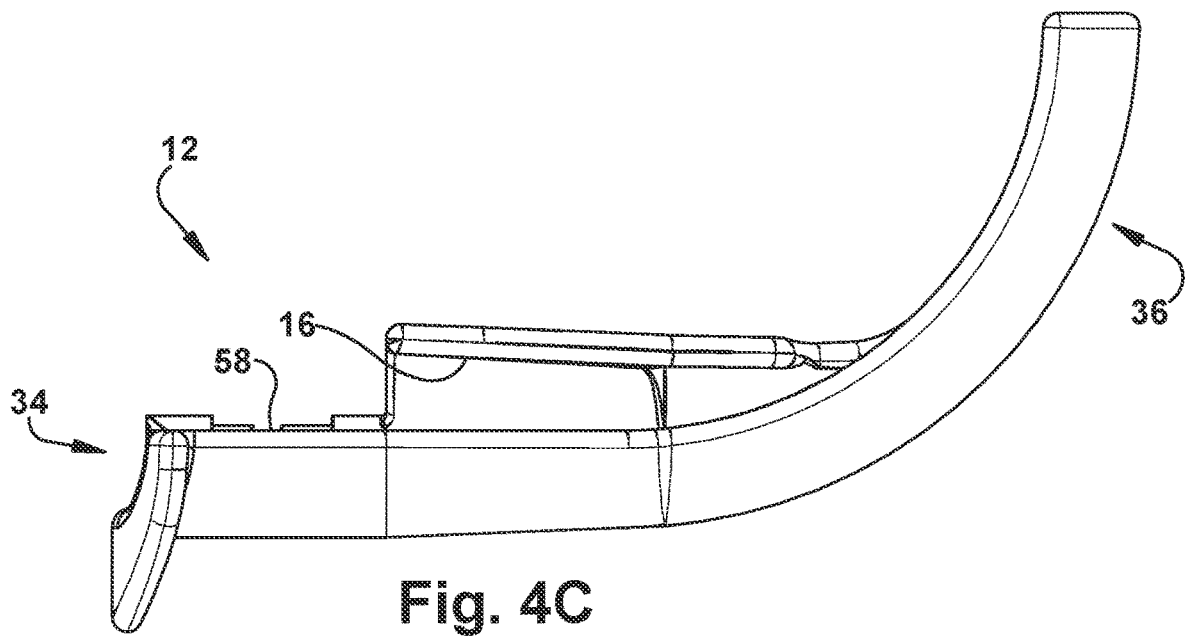
FIG. 4C is an opposing side view of the first component in FIG. 4B.
Figure 4D:
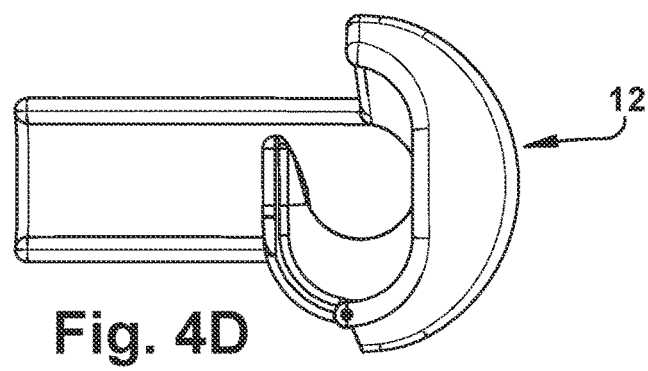
FIG. 4D is a top view of the first component in FIG. 4A.
Figure 5A:
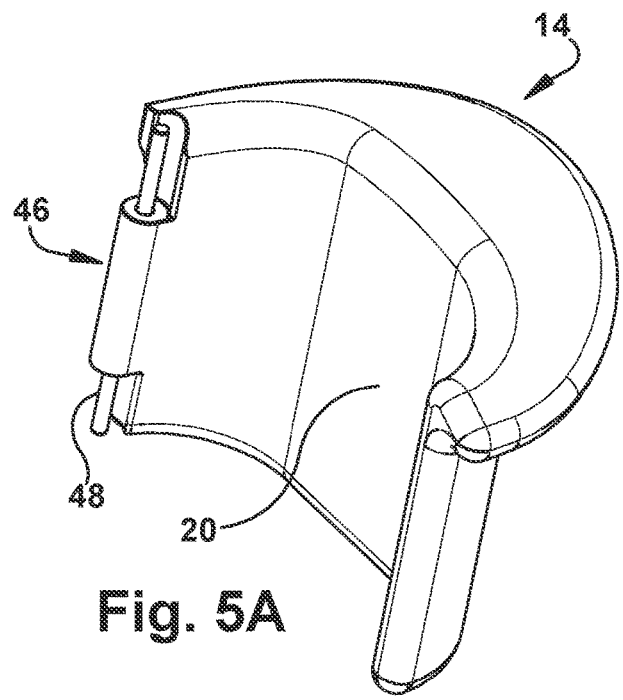
FIG. 5A is a perspective view showing a second component of the intubating airway in FIGS. 1A-C.
Figure 5B:
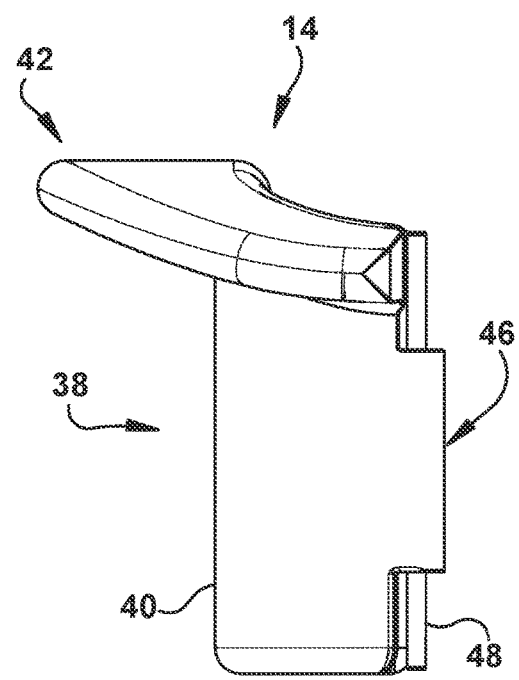
FIG. 5B is a side view showing the second component in FIG. 5A.
Figure 5C:
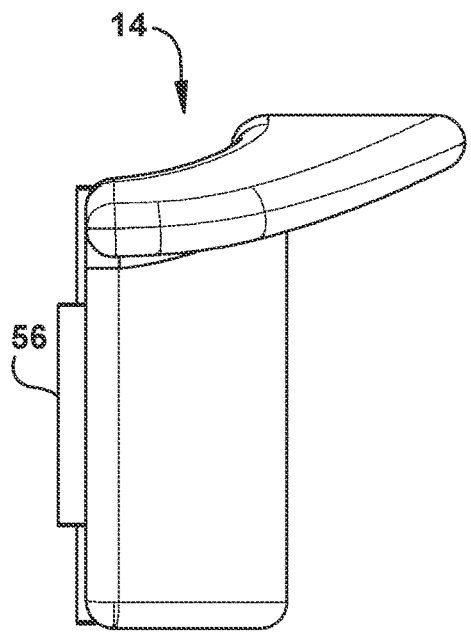
FIG. 5C is an opposing side view of the second component in FIG. 5B.
Figure 5D:
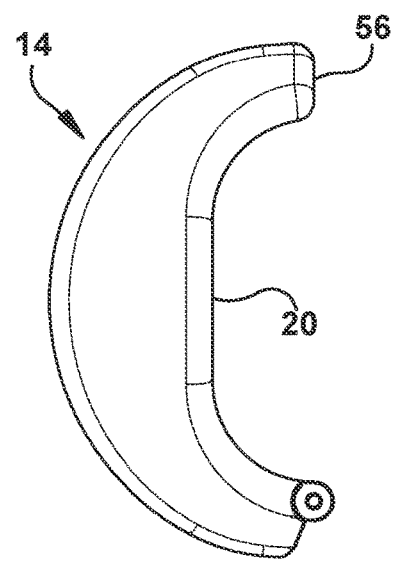
FIG. 5D is a top view of the second component in FIG. 5A.

Referring to FIGS. 1A-C, one aspect of the present disclosure can include an intubating airway 10. The airway 10 can comprise a first component 12 and a second articulating component 14 that are integrally formed together to form the airway. The first component 12 can have a first guiding surface 16 (FIG. 4C). The second articulating component 14 (FIGS. 1A-C) can be attached (e.g., directly attached) to the first component 12 via a hinge 18 (FIGS. 1B-C) and have a second guiding surface 20. In a closed configuration, the first and second guiding surfaces 16 and 20 can be flush with one another so that the first and second components 12 and 14 collectively define a conduit 22 (FIG. 2) having an interior passage that is dimensioned to direct a fiber-optic scope or an endotracheal tube extending through the interior passage for tracheal intubation. In an open configuration (FIG. 3), the first and second guiding surfaces 16 and 20 are not flush with one another so that no such conduit 22 is formed.

Referring specifically to FIGS. 4A-D, the first component 12 can include an anterior portion 24 and a posterior elbow portion 26. The anterior portion 24 can extend generally linearly in a longitudinal direction along a first extent and includes a first curved surface 28. The posterior elbow portion 26 can extend generally curvilinearly in the longitudinal direction and include a second curved surface 30 that defines a posterior curve. The posterior curve can direct a fiber-optic scope or endotracheal tube anteriorly toward the vocal cords during tracheal intubation. Furthermore, the second curved surface 30 of the posterior elbow portion and the first curved surface 28 of the anterior portion can together define a guiding surface of the airway 10. As also shown in FIGS. 4A-D, the first component 12 can include a longitudinal groove or slot 32 that extends between a proximal end 34 and a distal end 36 of the first component, and is sized and dimensioned to permit egress of a fiber-optic scope or endotracheal tube. In some instances, the width W (FIG. 4A) of the groove or slot 32 can be between about 4 mm to about 10 mm (e.g., about 7 mm). In one example, the width W of the groove or slot 32 is 7 mm. Advantageously, the longitudinal groove or slot 32 (in addition to the articulating second component 14) permits removal of the airway 10 from a subject without sliding the airway axially off of an endotracheal tube and also permits larger endotracheal tubes to be used.

FIGS. 5A-D illustrate the second articulating component 14. The second articulating component 14 can comprise a generally arcuate or arc-shaped body 38 having a first exterior surface 40 and the second guiding surface 20 located opposite the first exterior surface. The second articulating component 14 can also include a tab structure 42 that extends perpendicular, or substantially perpendicular to, the first exterior surface 40. The proximal end 34 (FIG. 1C) of the first component 12 also includes a similar or identical tab structure 44 that cooperates with the tab structure 42 (FIGS. 5A-D) as a means to withdrawn and advance the airway 10. The second articulating component 14 can also include a first hinge component 46 (FIG. 5A) that extends radially from a side wall 48 of the second articulating component. The first hinge component 46 can be sized and dimensioned to mate with a second recessed hinge component 50 (FIG. 4A) located in a side wall 52 of the first component 12. A pin 54 or other similar structure can extend axially through each of the first and second hinge components 46 and 50 to form the hinge 18 that joins the first and second components 12 and 14.

In another aspect, the second articulating component can include a leading edge 56 that, when the airway 10 is in the closed configuration, is in contact with a reciprocal edge 58 (FIG. 4C) of the first component 12 to define the conduit 22. And, in the open configuration, the leading edge 56 (FIG. 5C) is not in contact with the reciprocal edge 58 (FIG. 4C) so that no such conduit 22 is formed.

In another aspect, the first and second components 12 and 14, in the closed configuration, provide a continuous, uninterrupted exterior surface circumferentially surrounding the interior passage.

In another aspect, the second articulating component 14 remains directly connected to the first component 12 during an intubation procedure. In other words, the airway 10 is a single, unitary piece whose components 12 and 14 do not need to be separated during use in order to remove an endotracheal tube therefrom without disrupting the placement of the endotracheal tube.

In another aspect, the second articulating component 14 and the proximal end 34 of the first component 12 collectively form a mouth guard for abutting the exterior area of the mouth of a patient during endotracheal intubation and preventing the intubating airway 10 from overextending into the mouth of the patient. Advantageously, the mouth guard can serve as a built-in, rigid bite-block that protects a fiber-optic scope or endotracheal tube from damage by the patient during an intubation procedure.

In another aspect, the airway 10 can have a tapered or frusto-conical geometry when viewed from a first end 60 (FIG. 1A) to a second end 62 thereof. The tapered geometry advantageously eliminates discontinuities at the transition between the mouth guard and the remainder of the airway 10.

In another aspect, the airway 10 can include a latch mechanism (not shown). The latch mechanism can include one or more cooperating elements so that the first and second components 12 and 14, when the airway 10 is in the closed configuration, are retained in physical engagement with one another by the latch mechanism. Examples of latch mechanisms are known in the art can include for example, tongue and groove mechanisms, cooperating friction fit elements, and the like.

The airway 10 of the present disclosure overcomes several disadvantages of existing oral airway devices. For example, the modified Guedel airway, as disclosed by Rastogi, A. et al., *J Anaesthesiol Clin Pharmacol.* 2012 October-December; 28(4):542-543, is a standard Guedel airway with a strip taken from the convex surface of the outer portion of the airway and a strip taken from the contralateral internal bite block. It is used by placing the airway in the patient, advancing the fiberscope into the trachea, removing the airway, and then advancing the endotracheal tube. Unlike the airway 10 of the present application, it is a two-piece apparatus and must be removed before an endotracheal tube is advanced.

The airway disclosed in U.S. Pat. No. 8,631,795 is a modified soft airway with an integrated bite block that can be attached to an anesthesia circuit. It is not used to assist in endotracheal intubation, but rather ventilation of a conscious or semi-conscious patient.

U.S. Pat. No. 8,202,215 discloses a pharyngeal intubation guiding device. This device is not for use in awake fiberoptic intubation, and does not include any hinged structures that permit the device to be removed from a bronchoscope without disrupting the placement of an endotracheal tube.

U.S. Pat. No. 7,866,313 discloses an oral airway similar to a Williams airway but modified to have a separable, two-piece design. The disclosed device is differs from the airway 10 of the present application in that it does not have a single, integrated form with a hinge that permit the device to be removed from a bronchoscope without disrupting the placement of an endotracheal tube. The fact that the disclosed oral airway requires separating the oral airway into two pieces is disadvantageous because it creates the potential for loose pieces near the mouth of a patient, which is a safety risk.

In another aspect, the components 12 and 14 of the airway 10 can be constructed from medical grade low density polyethylene and have sufficient rigidity—or are reinforced—so as to prevent collapse when the airway is bitten down upon by a patient. In some instances, all or only a portion of the airway 10 can be latex-free.

It will be appreciated that airways of the present disclosure may be produced in a variety of sizes ranging from neonatal to large adult sizes. As such, the airways can be color-coded so as to indicate size upon quick visual observation.

Additionally, and/or alternatively, an airway 10 in accordance with the present disclosure may be adapted, configured, or manufactured to provide a desirable smell and/or taste. For example, a flavoring material may be applied during the manufacture of the airway 10, or may be applied afterwards, that results in a desirable flavor being experienced when the airway is utilized in the mouth. The flavor may be, for example, that of a food, a natural flavor, or an artificial flavor including, but not limited to, bubble gum or a fruit, such as an orange. Alternatively, or in addition, a material may be may be applied during the manufacture of the airway 10, or may be applied afterwards, that results in a desirable scent or odor being experienced when the airway is utilized. The scent or odor may be that of a food or other pleasant item. In connection with the flavoring and/or scent, the airway 10 may include a corresponding color, such as a pink color if the flavoring and/or scent is that of bubblegum.

Method

Figure 6:
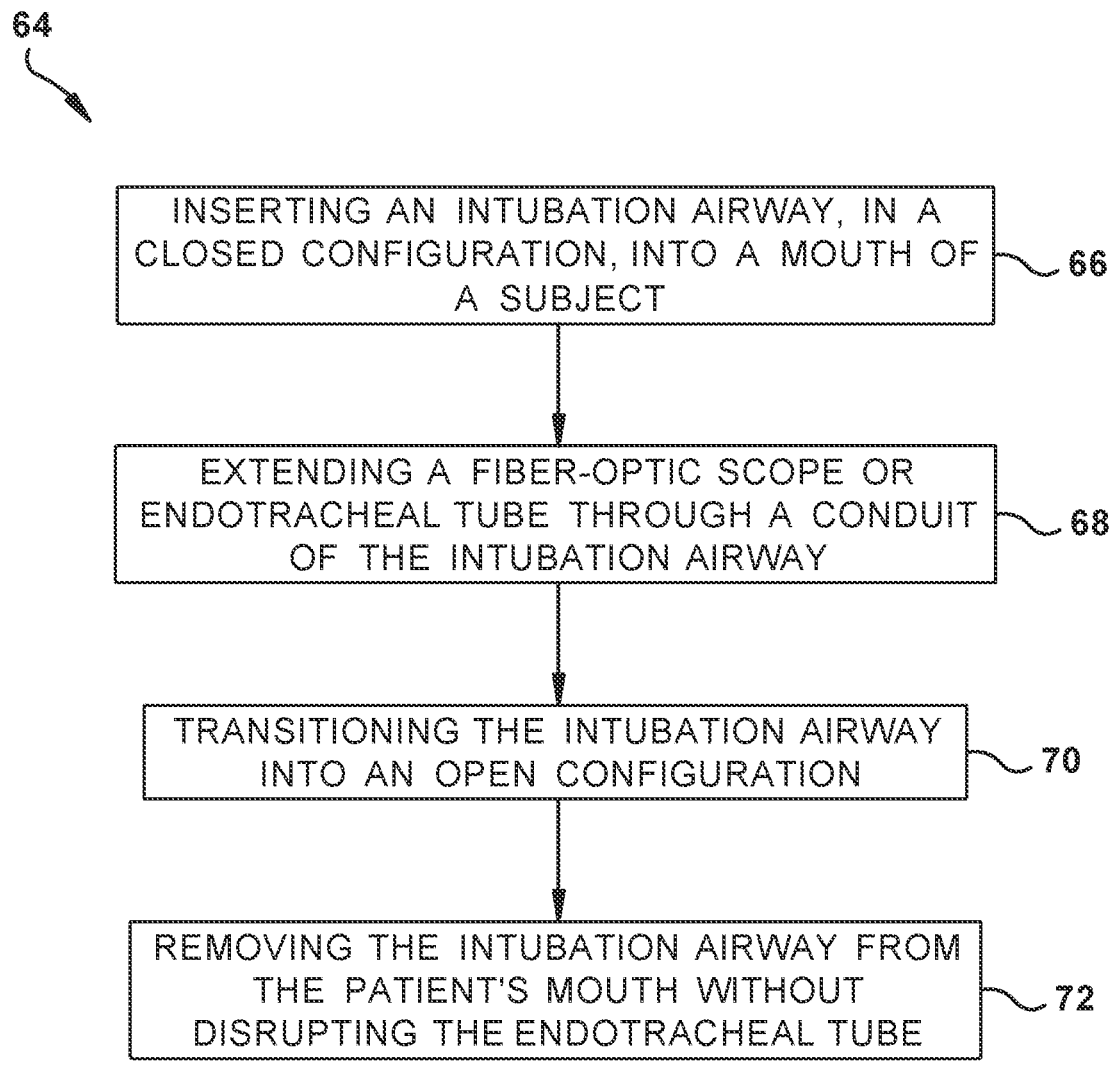
FIG. 6 is a process flow diagram illustrating a method for endoscopic tracheal intubation according to another aspect of the present disclosure.
Figure 7:
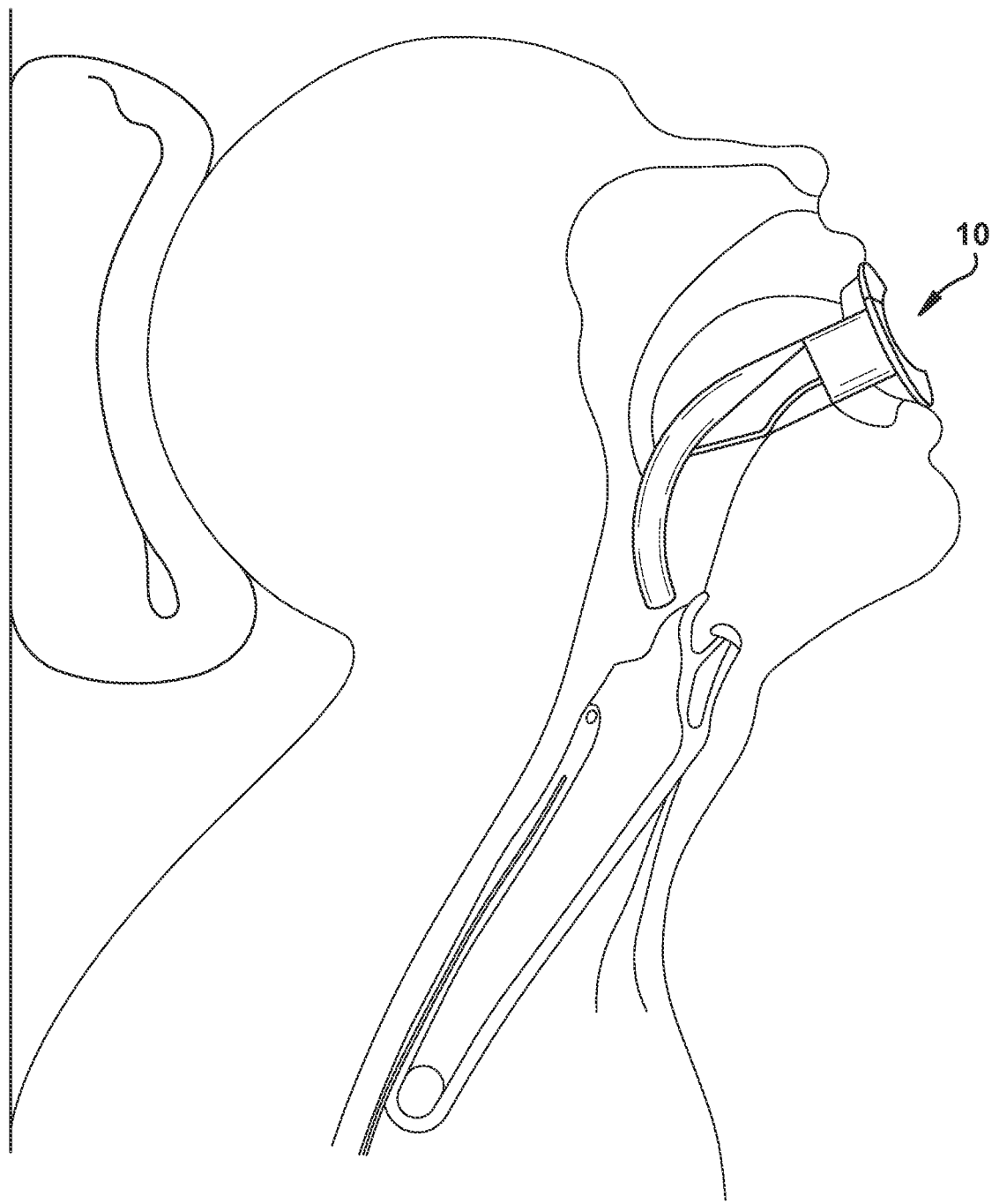
FIG. 7 is an illustration showing an intubating airway of the present disclosure, in the closed configuration placed in the mouth of a patient.
Figure 8:
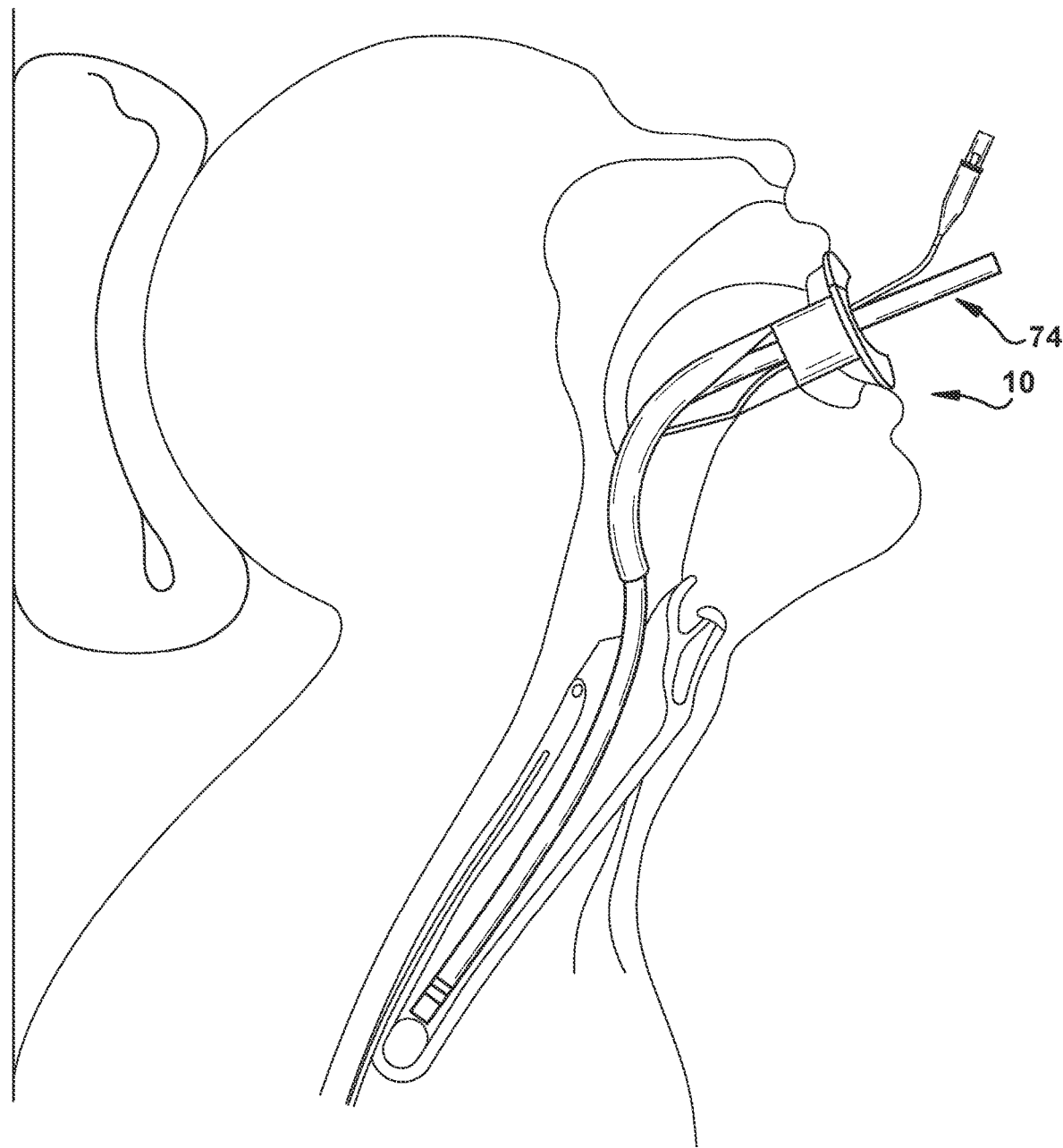
FIG. 8 is an illustration showing a fiber-optic scope advanced through the intubating airway and directed towards the trachea of the patient.
Figure 9:
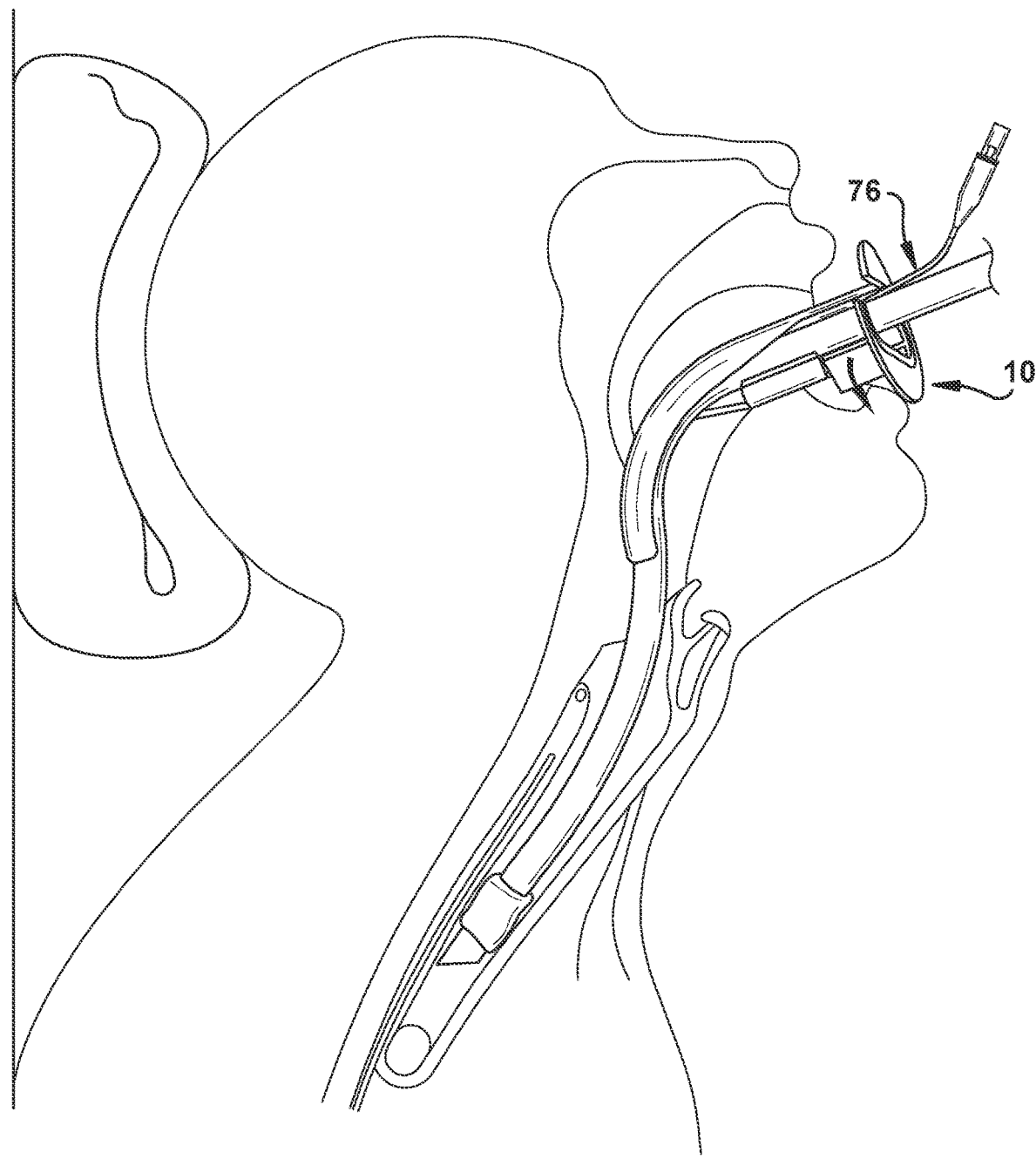
FIG. 9 is an illustration showing an endotracheal tube being advanced over the fiber-optic scope, through the intubating airway and into the trachea.
Figure 10:
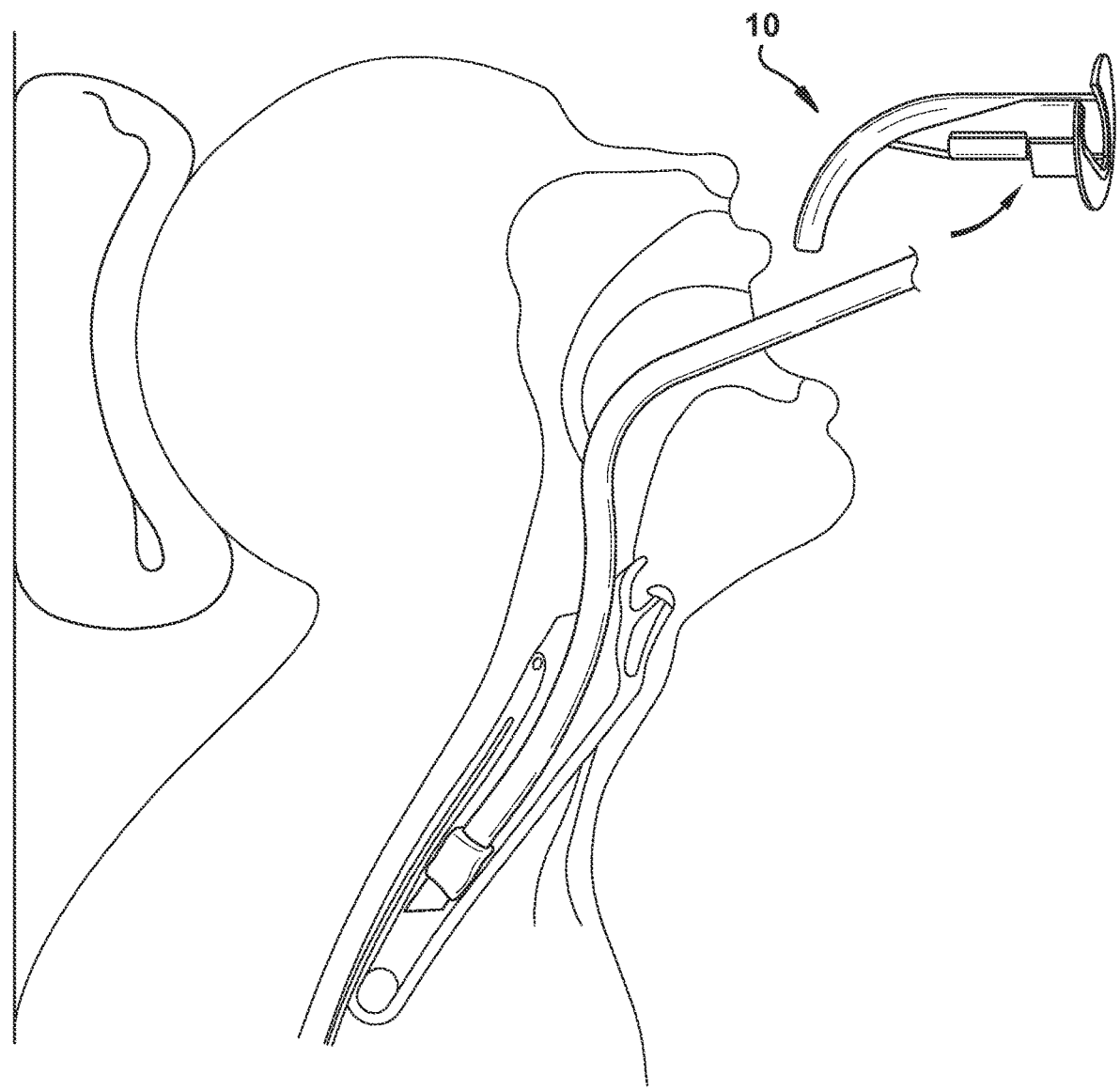
FIG. 10 is an illustration showing the intubating airway being peeled off the endotracheal tube without disturbing the endotracheal tube.

Another aspect of the present disclosure can include a method 64 (FIG. 6) for endoscopic tracheal intubation. As shown in FIG. 7, the method 64 can begin by placing an intubating airway 10, in the closed configuration, through the mouth and into the airway of a subject (Step 66). Next, at Step 68, a fiber-optic scope 74 (e.g., a bronchoscope) or an endotracheal tube 76 (FIG. 9) can be extended through the conduit 22 of the intubating airway 10. As shown in FIG. 8, a bronchoscope can be extended through the conduit 22. Next, an endotracheal tube 76 can be advanced over the bronchoscope (not shown for clarity), through the intubating airway 10, and into the trachea (FIG. 9). At Step 70, the intubating airway 10 can then be transitioned into the open configuration such that the first and second guiding surfaces 16 and 20 are not flush with one another and the conduit 22 is not formed. Then, as shown in FIG. 10, the intubating airway 10 can be removed from the patient's mouth without disrupting the endotracheal tube 76 (Step 72).

From the above description of the present disclosure, those skilled in the art will perceive improvements, changes and modifications. Such improvements, changes, and modifications are within the skill of those in the art and are intended to be covered by the appended claims. All patents, patent applications, and publications cited herein are incorporated by reference in their entirety.

The following is claimed:

1. An intubating airway comprising:
a first component having a proximal portion extending generally linearly in a longitudinal direction, a distal portion integral with the proximal portion and extending therefrom in a curved manner, and an open-ended channel extending along an entire length of the first component, the proximal portion having a first engaging sidewall; and
a second component pivotably connected to the first component such that the second component selectively pivots relative to the first component between closed and open configurations, the second component having a second engaging sidewall;
wherein, in the closed configuration, the first and second engaging sidewalls engage one another so that the second component closes the open-ended channel and forms a closed portion at the proximal portion of the first component while leaving a remainder of the open-ended channel open and uncovered by the second component, the first and second components at the closed portion of the open-ended channel collectively defining a conduit having an interior passage; and
wherein, in the open configuration, the first and second engaging sidewalls do not engage one another so that the open-ended channel is open along the entire length of the first component and the conduit is not formed.

2. The intubating airway of claim 1, wherein the first component has a first connecting sidewall having first hinge components, the first connecting sidewall and the first engaging sidewall being on opposite sides of the open channel, and wherein the second component has a second connecting sidewall spaced from the second engaging sidewall, the second connecting sidewall having second hinge components that cooperate with the first hinge components to form a hinge that pivotably connects the second component to the proximal portion of the first component.

3. The intubating airway of claim 1, wherein the interior passage of the conduit is dimensioned to direct a fiber-optic scope or an endotracheal tube extending through the interior passage for tracheal intubation.

4. The intubating airway of claim 1, wherein the curved distal portion is configured to direct a fiber-optic scope or endotracheal tube anteriorly toward the vocal cords during tracheal intubation.

5. The intubating airway of claim 1, wherein the first and second components, in the closed configuration, provide a continuous, uninterrupted exterior surface circumferentially surrounding the interior passage.

6. The intubating airway of claim 1, wherein the first and second components further comprise a mouth guard for abutting the exterior area of the mouth of a patient during endotracheal intubation and preventing the intubating airway from overextending into the mouth of the patient.

7. The intubating airway of claim 1, wherein the first component and the second component define a mouth guard of the oral airway when the intubating airway is in the closed configuration, the first component forming a first mouth guard portion and the second component forming a second mouth guard portion, with the first mouth guard portion and the second mouth guard portion defining the mouth guard.

8. The intubating airway of claim 1, further comprising a latch mechanism, wherein the first and second components, in the closed configuration, are retained in physical engagement with one another by the latch mechanism.

9. The intubating airway of claim 1, wherein the intubating airway has a substantially frusto-conical geometry that tapers from a first end of the intubating airway to a second end of the intubating airway.

10. The intubating airway of claim 1, wherein the second component remains directly connected to the first component during an intubation procedure.

11. A method for endoscopic tracheal intubation, the method comprising the steps of:
- extending a fiber-optic scope or an endotracheal tube through the conduit defined by the first component and the second component of the intubating airway of claim 1;
- transitioning the intubating airway into the open configuration after an endotracheal tube has extended through the conduit for tracheal intubation; and
- removing the intubating airway from the patient's mouth without disrupting the endotracheal tube.

12. The method of claim 11, wherein the first and second components completely encompass the endotracheal tube when extended through the conduit.

13. The method of claim 11, wherein the step of transitioning the intubating airway into an open configuration further comprises applying a sufficient amount of force to overcome a latch that serves to retain the first and second components together in the closed configuration.

14. An intubating airway intended to facilitate the guidance and insertion of an endotracheal tube using a fiber-optic scope, the intubating airway comprising:
- a first component having a first guiding surface, the first component including:
  - a proximal portion extending generally linearly in a longitudinal direction, the proximal portion including at a first end thereof a flat vertical face defining at least a portion of a mouth guard of the oral airway, the proximal portion having a first engaging sidewall,
  - a distal portion integral with the proximal portion and extending therefrom in a curved manner, and
  - an open-ended channel extending along an entire length of the first component, the open-ended channel being dimensioned to receive therethrough an endotracheal tube; and
- an second component pivotably connected to the first component such that the second component selectively pivots relative to the first component between closed and open configurations, the second component having a second engaging sidewall;
- wherein, in the closed configuration, the first and second engaging sidewalls engage one another so that the second component closes the open-ended channel and forms a closed portion at the proximal portion of the first component while leaving a remainder of the open-ended channel open and uncovered by the second component, the first and second components at the closed portion of the open-ended channel collectively define a conduit having an interior passage;
- wherein, in the open configuration, the first and second engaging sidewalls do not engage one another so that the open-ended channel is open along the entire length of the first component and the conduit is not formed; and
- wherein no such interior passage is formed in the open configuration so that the intubating airway may be removed from an endotracheal tube extending through the open-ended channel without having to pass any portion of the intubating airway over an end of the endotracheal tube.

15. The intubating airway of claim 14, wherein the first component has a first connecting sidewall having first hinge components, the first connecting sidewall and the first engaging sidewall being on opposite sides of the open channel, and wherein the second component has a second connecting sidewall spaced from the second engaging sidewall, the second connecting sidewall having second hinge components that cooperate with the first hinge components to form a hinge that pivotably connects the second component to the proximal portion of the first component.

16. The intubating airway of claim 14, wherein the interior passage of the conduit is dimensioned to direct a fiber-optic scope or an endotracheal tube extending through the interior passage for tracheal intubation.

17. The intubating airway of claim 14, wherein the first and second components, in the closed configuration, provide a continuous, uninterrupted exterior surface circumferentially surrounding the interior passage.

18. The intubating airway of claim 14, wherein the second component remains directly connected to the first component during an intubation procedure.

19. The intubating airway of claim 14, wherein the first component and the second component define the mouth guard of the oral airway when the intubating airway is in the closed configuration, the first component forming a first mouth guard portion and the second component forming a second mouth guard portion, with the first mouth guard portion and the second mouth guard portion defining the mouth guard.

20. A method for endoscopic tracheal intubation, the method comprising the steps of:
- extending a fiber-optic scope or an endotracheal tube through the conduit defined by the first component and the second component of the intubating airway of claim 14;
- transitioning the intubating airway into the open configuration after an endotracheal tube has extended through the conduit for tracheal intubation; and
- removing the intubating airway from the patient's mouth without disrupting the endotracheal tube.

* * * * *